United States Patent
Fulton, III

(10) Patent No.: US 8,740,961 B2
(45) Date of Patent: Jun. 3, 2014

(54) METHOD FOR TREATING A TARGET SITE IN A VASCULAR BODY CHANNEL

(76) Inventor: Richard Eustis Fulton, III, Grand Junction, CO (US)

( * ) Notice: Subject to any disclaimer, the term of this patent is extended or adjusted under 35 U.S.C. 154(b) by 152 days.

(21) Appl. No.: 12/813,339

(22) Filed: Jun. 10, 2010

(65) Prior Publication Data

US 2011/0040319 A1 Feb. 17, 2011

Related U.S. Application Data

(60) Provisional application No. 61/277,154, filed on Sep. 21, 2009, provisional application No. 61/274,165, filed on Aug. 13, 2009.

(51) Int. Cl.
*A61F 2/06* (2013.01)

(52) U.S. Cl.
USPC .................... 623/1.11; 604/101.03

(58) Field of Classification Search
USPC ............... 606/191–200; 604/96.01, 604/101.01–101.03; 623/1.11–1.16
See application file for complete search history.

(56) References Cited

U.S. PATENT DOCUMENTS

| | | |
|---|---|---|
| 3,799,172 A | 3/1974 | Szpur |
| 4,921,478 A | 5/1990 | Solano et al. |
| 5,011,488 A | 4/1991 | Ginsburg |
| 5,059,178 A | 10/1991 | Ya |
| 5,449,372 A | 9/1995 | Schmaltz et al. |
| 5,462,529 A * | 10/1995 | Simpson et al. ......... 604/101.04 |
| 5,709,701 A * | 1/1998 | Parodi ........................ 606/194 |
| 5,843,022 A | 12/1998 | Willard et al. |
| 5,879,380 A | 3/1999 | Kalmann et al. |
| 6,022,336 A * | 2/2000 | Zadno-Azizi et al. ... 604/101.05 |
| 6,221,006 B1 | 4/2001 | Dubrul et al. |
| 6,238,412 B1 | 5/2001 | Dubrul et al. |
| 6,409,742 B1 | 6/2002 | Fulton, III et al. |
| 6,450,989 B2 | 9/2002 | Dubrul et al. |
| 6,575,932 B1 * | 6/2003 | O'Brien et al. .......... 604/101.01 |
| 6,626,861 B1 * | 9/2003 | Hart et al. .................. 604/96.01 |
| 6,635,068 B1 | 10/2003 | Dubrul et al. |
| 6,652,505 B1 | 11/2003 | Tsugita |
| 6,699,260 B2 | 3/2004 | Dubrul et al. |
| 6,706,013 B1 * | 3/2004 | Bhat et al. .................. 604/96.01 |
| 6,733,519 B2 | 5/2004 | Lashinski et al. |
| 6,852,097 B1 | 2/2005 | Fulton, III |
| 7,011,654 B2 | 3/2006 | Dubrul et al. |
| 7,232,432 B2 | 6/2007 | Fulton, III et al. |
| 7,331,980 B2 | 2/2008 | Dubrul et al. |
| 2002/0169436 A1 * | 11/2002 | Gurm et al. ................ 604/509 |
| 2005/0240145 A1 * | 10/2005 | Scott et al. .................. 604/20 |
| 2005/0251246 A1 * | 11/2005 | Dubrul et al. .............. 623/1.42 |

* cited by examiner

*Primary Examiner* — Darwin Erezo
*Assistant Examiner* — Katrina Stransky
(74) *Attorney, Agent, or Firm* — Wilson Sonsini Goodrich & Rosati

(57) ABSTRACT

A method of treating a target site within a vascular channel of the body uses a catheter assembly having proximal and distal occluders which are positioned in occluding states at positions proximal and distal of a target site to define an occluded region therebetween. An agent is injected into the region. An intervention is performed at the target site while the vessel is occluded and the agent is in the region. The catheter assembly is removed from the channel. Intervention may include expanding a balloon within a temporary stent structure against the channel, collapsing balloon and then removing the collapsed balloon and stent structure from the channel. A balloon stent assembly comprises a catheter assembly, a temporary stent surrounding a balloon, the temporary stent placeable in a contracted state by the catheter assembly and in an expanded state by inflation of the balloon.

14 Claims, 9 Drawing Sheets

METHOD FOR TREATING A TARGET SITE IN A VASCULAR BODY CHANNEL

CROSS-REFERENCE TO OTHER APPLICATIONS

This application claims the benefit of U.S. provisional patent application No. 61/274,165 filed on 13 Aug. 2009 and U.S. provisional patent application No. 61/277,154 filed on 21 Sep. 2009, the disclosures of which are incorporated by reference.

This application is related to my U.S. Pat. No. 6,238,412, the disclosure of which is incorporated by reference.

FEDERALLY SPONSORED RESEARCH OR DEVELOPMENT

None.

BACKGROUND OF THE INVENTION

Balloon angioplasty has been a popular method of treating vascular occlusions since 1976. With plain old balloon angioplasty (POBA), there exists a significant subset of patients who have immediate suboptimal results related to the trauma to the vessel including dissection of the vessel, incomplete plaque compression, poor lumen gain, and acute elastic recoil of the vessel, amongst others. Because of these suboptimal immediate results, other means to treat vascular stenosis were developed. Intravascular stents are widely utilized, addressing the acute problems of angioplasty and reducing the restenosis rates from 50-60% for POBA to 30-35% for these bare metal stents (BMS).

Because the restenosis rates of BMS are usually unacceptable, drug eluting stents (DES) are used to inhibit restenosis. These devices reduce the restenosis rate to around 20% and lower in the coronary circulation. However, DES are extremely expensive and can lead to thrombosis, which can prove fatal. In addition, DES are not particularly effective in the peripheral circulation. The expense of drug eluting stents at over $3000 each dramatically increases the overall cost of healthcare in the U.S. Finally, not only are the stents are costly, but expensive and potentially harmful drugs are routinely used for at least a year after stent implantation.

It is apparent that restenosis is the Achilles heel of all vascular intervention, from angioplasty to stenting and even surgery. However, it is clear than drugs can prevent restenosis. The primary question is how best to deliver the drugs in the most cost effective manner available while producing good patient outcomes and preventing complications.

Because of the variable plaque morphology and composition, stresses provided by conventional POBA are unpredictable, and frequently high pressure balloon inflations are needed to successfully provide enough stress to crack the plaque. When the plaque does compress at high pressures, the balloon will very rapidly expand to its full dimension in a noticeable pop (tenths of a second), very rapidly expanding the vessel wall often rupturing the smooth muscle cells. Dissection frequently occurs, as does irreparable injury to the smooth muscle cells which do not have the chance to gradually stretch and deform to maintain their integrity.

Therefore, methods and devices that lower the pressure at which the plaque will fracture will produce a slower and more gradual stretching of the arterial wall. This slower stretching will diminish the degree of trauma to the vessel.

A wire or wires along the outside of an angioplasty balloon, sometimes called buddy wires, produces focal areas of stresses along the wires that were approximately 120 times that of a conventional balloon surface, and the stress patterns from the external wire extends into the plaque rather than being concentrated on the surface as with a conventional balloon. The stress patterns are less dependent on the morphology and composition of the plaque than with conventional balloons. In other words, the stresses are more predictable, concentrated, and required lower balloon pressures to compress the plaque. Clinical studies confirmed that when compared to conventional POBA catheters, the buddy wire technique compressed the plaque at lower balloon pressures, caused fewer dissections, had less elastic recoil, and had more lumen gain, as well as a trend toward lower restenosis rate.

More recently, cutting and scoring balloons have been introduced extending these concepts. One such balloon uses several razor type blades along the balloon margins. Scoring balloons utilize several 0.005 to 0.007 inch struts placed over a balloon. Both balloon types are commercially successful. They are typically used in treating complex lesions or in plaque modification. The scoring balloon has been shown to achieve 50% more lumen gain than POBA when utilized as predilatation before stent implantation. This procedure significantly reduces the number of dissections when compared to POBA. The scoring balloon also has been shown to not slip off of the lesion, which is a problem with POBA. The scoring balloon is also more effective in soft, fibrous, and calcified plaques than POBA and has been recommended as a strategy of plaque modification in treating complex lesions. The use of the scoring balloon has thus resulted in very low incidences of inadvertent or unplanned stenting, commonly referred to as bail out stenting.

Prolonged inflation times improve the immediate results of POBA with fewer dissections, fewer further interventions such as stenting, and less restenosis. On the other hand other studies did not show improvement in long term results with prolonged inflation times, possibly because their prolonged inflations were the result of treating dissections. Applicant is unaware of any studies that evaluate both plaque modification and prolonged inflation times.

While these mechanical strategies have resulted in measurable improvement in the acute complications of POBA, the most promising advancement in POBA has been the advent of drug eluting balloons (DEB's). A DEB is a POBA balloon coated with an antiproliferative drug, such as paclitaxel. The drug is delivered during the rather short balloon inflation and is present in smooth muscle cells up to six days later. The drug from a DEB covers essentially 100% of the plaque/vessel wall vs. only 15-20% with drug eluting stents. Compared to DES in treating coronary in-stent restenosis, a DEB seems preferable. In the THUNDER trial (sponsored by University Hospital Tuebingen, Tuebingen, Germany, reported in The New England Journal of Medicine, volume 358:689-699, Feb. 14, 2008, Number 7), a DEB was compared to POBA in the peripheral vasculature. DEB was very effective, and at 2 years the target lesion revascularization rate was only 15% with the DEB vs. 59% with POBA. Most experts in the field expect the general usage results of DEB's in coronary circulation to be in the range of drug eluting stents, i.e., a restenosis rate of around 20% or so. This rate leaves considerable room for improvement.

Therefore, both mechanical and pharmacological strategies have shown advantages in treating vascular lesions with balloon angioplasty. The mechanical strategies effectively address the acute or immediate problems by causing less injury to the vessel and the pharmacological strategy of drug eluting balloons significantly diminish restenosis.

Moreover, recent experiments have demonstrated that infusion of paclitaxel, an antiproliferative drug, directly into the artery may be just as effective as drug eluting balloons or drug eluting stents. This is usually done by employing a catheter specifically designed for infusion of a drug over the site of the angioplasty or stent placement after the angioplasty and/or stent placement. This type of catheter usually has two balloons, one proximal and one distal. The drug or other agent is infused between the two in a closed system, drug infusion performed after the angioplasty, stent placement or other therapeutic procedure. This requires removal of the angioplasty balloon or stent delivery catheter, which is utilized prior to the drug delivery, and subsequent placement of a separate device to deliver the drug. This is problematic not only because of the cost of the extra device, but also platelets adhere over the fissures in the plaque and about the small areas of injury in the arterial wall while the exchange is taking place, preventing some of the drug from being delivered to the wall where it is needed. Additionally, by just infusing a drug into a space that has been previously dilated, there is very little pressure forcing the drug into the wall. Subsequent to the therapeutic procedure and the drug delivery steps, the drug is then released downstream.

In U.S. Pat. No. 5,059,178, Ya et al. describe a device with a downstream balloon catheter blocking element and an upstream suction catheter with a balloon blocking element for the removal of thrombus from a blood vessel. The device is utilized to dissolve the thrombus by injecting a dissolving agent into the space between the two balloons and then withdraw the dissolved thrombus from the body through upstream suction catheter. Any subsequent intervention or therapy (angioplasty, stent placement, and the like) are performed after the removal of the dissolved thrombus.

In U.S. Pat. No. 6,022,366, Zadno-Azizi et al. describe another double balloon device similar to one described by Ya above but is directed toward embolic containment. This device is actually a three catheter irrigation/aspiration system and also has an innermost downstream balloon blocking or occluding element and an outermost upstream balloon occlusion catheter with an intermediate catheter between the two. The irrigation/aspiration of debris and emboli occurs by use of the outer pathway between the upstream balloon occlusion catheter and the intermediate catheter, and by the use of the inner pathway between the intermediate catheter and the innermost downstream balloon blocking element. The use of three catheters tends to reduce the cross-sectional size of the pathway available for aspiration of material.

In U.S. Pat. No. 5,449,372, Schmalz et al. describe a temporary stent that can be used for support after dilatation of the lesion.

BRIEF SUMMARY OF THE INVENTION

To address the problem of how best to deliver the drugs in the most cost effective manner available while producing good patient outcomes and preventing complications, the medical device industry has essentially focused on developing methods and devices that inhibit the vascular response to the injury (restenosis), as opposed to developing a device that causes less injury, and hence less restenosis. One aspect of the present invention is directed to a device and method that both causes less injury to the vasculature by the use of dilatation of a braid over a balloon causing less dissection and more even plaque disruption at lower pressures and introduces drug deep within the vessel wall; this latter act is accomplished by using proximal and distal occluders, injecting an agent, such as an anti-proliferative drug, into the region between the occluders, and performing an intervention, such as balloon angioplasty, while the occluders and injected agent remain in place. Another aspect of the invention also helps to maintain pressure upon the vessel wall similar to prolonged balloon inflation by using a braided, stent like structure as a temporary or transient stent. Thus less initial injury and less elastic recoil should result in less restenosis, and delivering a drug will further reduce or prevent the restenosis.

It is the immediate result of an intervention (the immediate lumen diameter and the immediate residual percent stenosis) that typically determines the late outcome after coronary or other vascular intervention. The present invention is designed to improve these two factors. An optimal outcome in percutaneous interventions depend upon: 1) obtaining an excellent acute angiographic results with less dissection and elastic recoil, 2) avoiding damage to the distal vascular bed (as with atherectomy), and 3) reducing smooth muscle cell proliferation with pharmacological intervention. The invention addresses all three areas.

A first example of the invention is directed to a method of treating a target site within a vascular channel of the body using a catheter assembly, the catheter assembly comprising a proximal occluder and a distal occluder. The method includes the following steps. The proximal occluder is positioned in a vascular channel-occluding state within the vascular channel at a first position proximal of a target site thereby occluding the vascular channel at the first position. The distal occluder is positioned in a vascular channel-occluding state within the vascular channel at a second position distal of a target site thereby occluding the vascular channel at the second position and thereby defining a region between the distal and proximal occluders. An agent is injected into the region. An intervention is performed at the target site while the distal and proximal occluders are in their vascular channel-occluding states and the agent is in the region. The catheter assembly is removed from the vascular channel.

In some examples the intervention performing step comprises expanding an expansion device, such as a balloon and a temporary stent structure covering the balloon, against an inner wall of the vascular channel. In some examples the balloon is collapsed leaving the stent structure expanded against the inner wall for a period of time, and the collapsed balloon and the collapsed stent structure are removed from the vascular channel during the stent structure removing step.

An example of a balloon stent assembly comprises a catheter assembly having a proximal portion and a distal portion. The catheter assembly comprises first and second elongate members. A temporary stent has proximal and distal ends; the proximal end is secured to a first position along the first elongate member and the distal end secured to a second position along the second elongate member, the temporary stent placeable in a contracted state by movement of the first and second positions away from one another. The assembly also includes an inflatable balloon mounted to the distal portion of the catheter assembly at a location surrounded by the temporary stent. The balloon is placeable in an inflated state, thereby placing the temporary stent in an expanded state, and in a collapsed state. The temporary stent is free to remain in the expanded state when the balloon moves to the collapsed state.

By utilizing the balloon to expand the temporary stent, not only the pressure of the balloon is brought to bear on the obstruction, but its actions are enhanced by the overlying temporary stent structure. The wires of the temporary stent provide areas of focal force on the plaque that will allow the plaque or obstruction to be dilated with less pressure creating a controlled expansion compared to the uncontrolled rupture and dissections frequently seen with POBA. There will be a more gradual stretching and more gradual deforming of the smooth muscle cells, and they will have an opportunity to accommodate this stretching and maintain their integrity rather than being irreparably injured as is frequently the case with POBA. Therefore the balloon serves two distinct functions: 1) It dilates the plaque or obstruction (and in a more consistent manner because of the overlying temporary stent structure), and 2) It dilates the temporary stent more effectively, with more force, and with more lumen gain than could be achieved by dilating the temporary stent structure without the assistance of the balloon. Therefore together the balloon along with the temporary stent will be able to effectively dilate and then support the dilated vessel subsequent to the dilatation.

In some examples the first elongate member comprises an outer, actuator sleeve and the second elongate member comprises an inner, balloon catheter shaft to which the balloon is mounted. In some examples the temporary stent comprises a porous braided stent structure.

Treating advanced vascular disease is one of the largest health care expenses born by society. There are projected to be one million non-coronary angioplasties and 900,000 stand alone coronary angioplasties in 2012. (Millennium Research Group, 2009. American Heart Association, Heart Disease and Stroke Statistics, 2009 Update at a Glance.) These simpler, less expensive interventional methods, such as POBA, are frequently not effective, necessitating the use of more complex and expensive alternatives, such as stenting and surgery, which cost billions of dollars each year.

The use of the present invention is expected to improve on the results of POBA and reduce or avoid the need for stenting and/or surgery, by causing less vascular injury initially, preventing elastic recoil that frequently demands stenting, and preventing restenosis by simultaneously administering a non-proliferative agent. A procedure conducted according to the present invention is expected to cost only marginally more than POBA.

A rough calculation shows that the use of the present invention could result in large cost savings of over $1 billion per year as approximately 1.9 million peripheral angioplasties and stand alone coronary angioplasties (not associated with stent implantation) will be performed in 2012. (Millennium Research Group, 2009. American Heart Association, Heart Disease and Stroke Statistics, 2009 Update at a Glance.) By replacing POBA with the present invention in all cases, and diminishing the re-intervention rate from 40% of 1.9 million patients (760,000 patients) to 10% (190,000 patients), approximately 570,000 patients would be spared re-intervention. At a Medicare reimbursement cost of $5850/procedure, there would be savings of $3.33 billion/year. Currently, such restenotic lesions are usually treated with stents, surgery, or other more costly methods. On average, these added procedures add a cost of about $2,000 for each procedure. If the $2000 is added to each re-intervention in 80% of these cases, then the savings are increased by $912 million (570,000 procedures×80%×$2000=$912 MM), for a total possible savings of $4.24 billion per year. A market penetration of 25% would result in yearly cost savings of over $1 billion per year, not even considering the expected diminished incidence of costly "bail out" or unanticipated stenting when using the present invention.

Other features, aspects and advantages of the present invention can be seen on review the figures the detailed description, and the claims which follow.

BRIEF DESCRIPTION OF THE DRAWINGS

FIG. 1 is a mechanical schematic showing the device fully deployed in a Dacron® graft used in hemodialysis. The FIG. 1 drawing shows the blocking element at the distal end of the catheter in its radially expanded state and the occlusion engaging element at the distal end of the support wire in its radially expanded state. It is important to note that the proximal blocking element may take a variety of shapes as would be required for the particular application. The preferred shape is likely to be a funnel shape where the larger diameter is distal to the lesser diameter that is proximal on the element. This funnel shape allows the obstruction to be more easily accepted into the catheter due to the pull/push of the engaging element, aspiration or both.

FIG. 2 is a longitudinal view of the distal portion of the support wire with a braided occlusion engaging element in its radial compressed state. This is the state where the support wire and engaging element can be inserted through the occlusion that is to be removed.

FIG. 3 shows the FIG. 2 braided occlusion engaging element in its radially expanded state, which is the state shown in FIG. 1.

FIG. 4 shows the multi-wing malecot type blocking element at the distal end of the catheter in its radially expanded state, which is the state shown in FIG. 1. It should be noted that the scale of the FIG. 4 catheter is much reduced compared to the scale of the occlusion removal wire and braided element shown in FIGS. 2 and 3.

FIG. 5 is a longitudinal view, in partial cross-section, showing the catheter and dilator with a ferrule at the distal tip of the guide wire in a passageway having an occlusion that is to be removed.

FIG. 6 shows the next step in which the dilator is being removed thereby causing the malecot type blocking mechanism to become expanded by virtue of pressure against the distal end of the catheter tip of the dilator.

FIG. 7 shows the next step in which the support wire together with the braided occlusion removal element in its radially compressed state (the state shown in FIG. 2) is inserted through the catheter and through the occlusion to be removed.

FIG. 8 shows the next step in which the braided occlusion removal element has been expanded and is being pulled in a proximal direction thereby forcing the occlusion into the catheter for removal with or without aspiration.

FIG. 9 shows the multi-wing malecot type blocking element at the distal end of the catheter in its radially expanded state.

FIG. 10 shows the shape of the expansion resulting from the malecot type blocking element shown in FIG. 9.

FIG. 11 is an enlarged simplified partial cross-sectional view of a catheter assembly made according to the invention with the balloon expanded at a target site.

FIG. 12-17 show the various steps in the use of the catheter assembly of FIG. 11.

FIGS. 18-20 show another example of a catheter assembly in which a removable, expandable braid, acting as a stent like structure, is positioned over the balloon, with the balloon and the braided stent-like structure both in expanded states in FIG. 18, with the braided stent like structure in an expanded state and the balloon in a collapsed state in FIG. 19, and the balloon and a braided stent like structure both an collapsed states in FIG. 20.

DETAILED DESCRIPTION OF THE INVENTION

Figure 1:
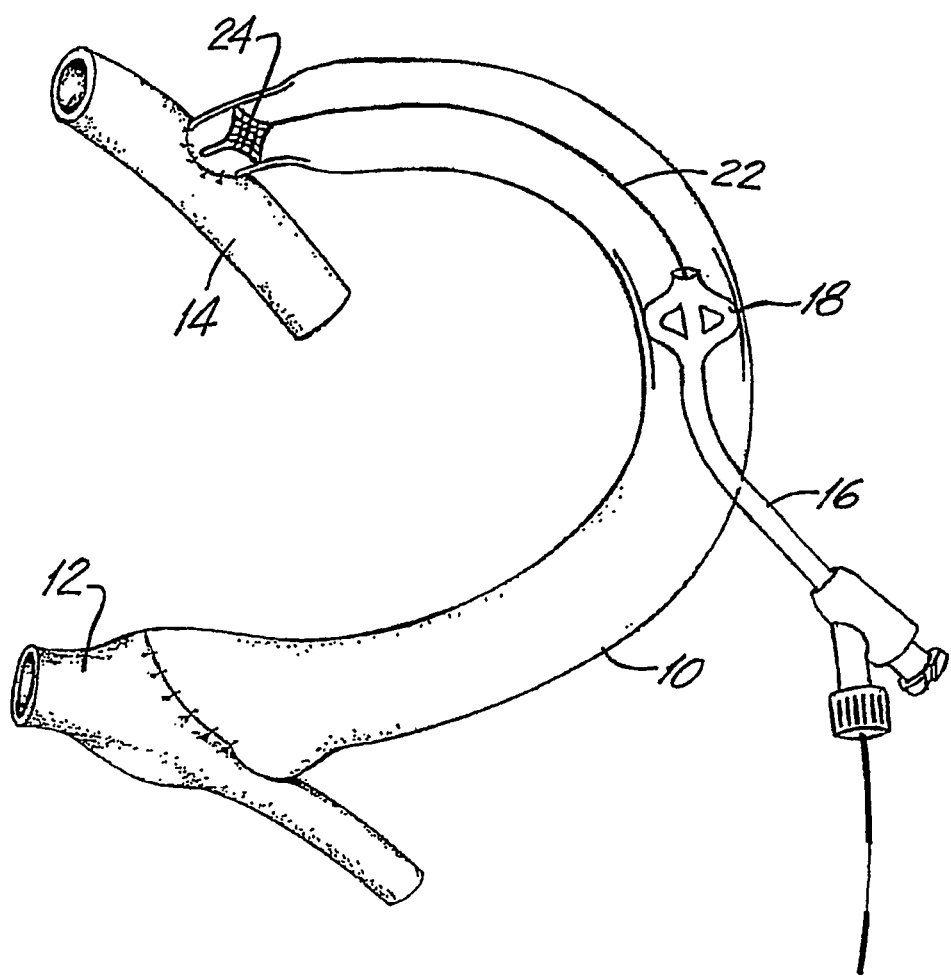
FIGS. 1-10 disclose conventional structures as shown in my U.S. Pat. No. 6,238,412.

The following description will typically be with reference to specific structural embodiments and methods. It is to be understood that there is no intention to limit the invention to the specifically disclosed embodiments and methods but that the invention may be practiced using other features, elements, methods and embodiments. Preferred embodiments are described to illustrate the present invention, not to limit its scope, which is defined by the claims. Those of ordinary skill in the art will recognize a variety of equivalent variations on the description that follows. Like elements in various embodiments are commonly referred to with like reference numerals.

FIG. 1 shows a typical synthetic graft 10 used in hemodialysis. The graft extends between a vein 12 and an artery 14. The graft 10 may be about thirty centimeters long with an inner diameter (I.D.) of 6 or 7 millimeters. A catheter 16 is inserted through the wall of the graft or vessel. Typically the catheter might have an outside diameter (O.D.) of 2.7 mm and an inner diameter (I.D.) of 2.3 mm A malecot type expansion device 18 is covered with a membrane 20 (see FIG. 4). When expanded, it serves to block the annular space between the outside wall of the catheter 16 and the graft 10. A support wire 22 for a braided removal mechanism 24 will typically have an outside diameter of about one mm and has an internal actuator rod 26 (see FIG. 2) of approximately 0.5 mm. Because of the simplicity of the design, this outside diameter could be smaller than 0.5 mm. In FIG. 1, the malecot type blocking device 18 and the braided removal device 24 are both shown in their expanded state and are positioned so that retrograde or proximal movement of the support wire 22 will pull the braided element in a proximal direction to push out whatever coagulated blood is between the braided device 18 and the distal end of the catheter into the catheter opening where it can be aspirated; thereby clearing the blockage in the graft or other vessel.

In one example of the structure of FIG. 1, which has been partly tested, was designed for use in a hemodialysis graft 10 having an I.D. of approximately six to seven mm. In that case, the catheter 16 has an 8 French O.D. (2.7 mm) and a 7 French I.D. (2.3 mm). The support wire 22 is a fairly standard movable core guide wire of 35 mils (that is, 0.35 inches, which is slightly under 1 mm). The actuator rod 26 in the support wire is approximately 15 mils and thus slightly under 0.5 mm. The braided element 24 has an insertion diameter that is approximately one mm and expands to cover the seven mm diameter of the graft. In order to achieve this seven fold increase in diameter, the braided element has a length of 11 to 13 mm. Thus, the catheter has an annulus of about 2.3 mm around the support wire, through which annulus the blood occlusion is aspirated.

Figure 2:
Figure 3:
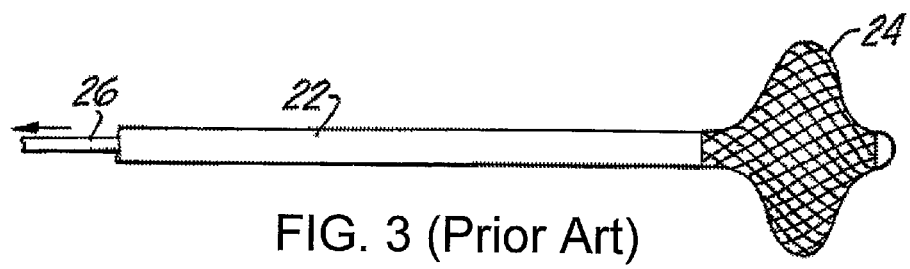

FIGS. 2 and 3 illustrate the support wire 22 and braided element 24 which constitute the occlusion engaging element that is moved proximal to push the occlusion into the catheter for removal. A preferred occlusion engaging element 24 is a braided element. The braided material has to have a stiffness such that it will not collapse or fold under the pressure of the occlusion when this engaging element is being moved proximally. Yet the filaments that form the braid must be flexible enough to be moved between the two states as shown in FIGS. 2 and 3. Materials from polyester to stainless steel can be successfully used.

The distal tip of the braided element 24 is connected to the distal tip of the actuator rod 26. The proximal edge of the braided element 24 is bonded to the distal end of the support wire 22. Thus when the actuator rod 26 is pushed in a distal direction relative to the wire 22, the braided device is forced into its collapsed state shown in FIG. 2 and is available to be pushed through the catheter and through or around the occlusion which is to be removed. When this engaging element 24 has been fully inserted, the actuator rod 26 is moved in a proximal direction causing the braided element 24 to take the expanded position such as that shown in FIG. 3 so that subsequent movement of the entire support wire 22 will cause the braided element to move against the occlusion and push the occlusion into the distal end of the catheter. In some circumstances, the braided element 24 might be left as a braid with openings because the portions of the occlusion which may pass through the openings will be sufficiently smaller liquids so that they do not have to be removed. In other circumstances, it might be desirable to cover the braided element 24 with a membrane or film so that it becomes substantially impermeable. Further the membrane or film covering the engaging element will be helpful in preventing trauma to the inner walls of native tissue. Even further, this membrane may be helpful in optimizing the physical characteristics of the engaging element.

With reference to FIG. 1, it might be noted that when the braided element is pushed all the way down to one end of the graft 10, as shown in FIG. 1, and then expanded it will be expanding against a portion of the wall of the graft that is smaller than the bulk of the graft. However, as the support wire 22 is pulled to move the braided occlusion removal element proximally, the braided occlusion element rides on the wall of the graft and will expand as the wall of the graft expands as long as tension is maintained on the actuator rod 26.

Figure 4:
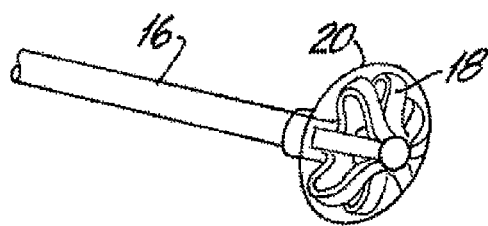
Figure 5:
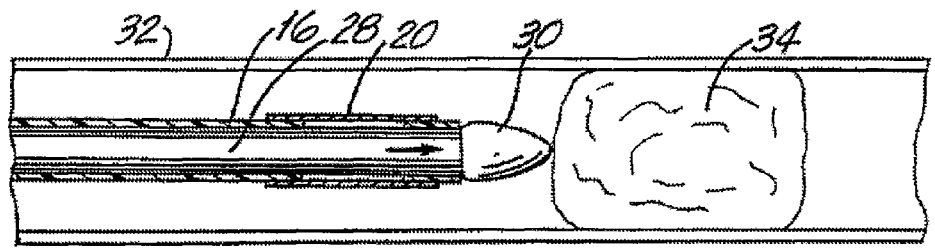

There might be applications of the invention where the passageway involved is a tissue passageway such as a blood vessel or other channel within the body, where this braided element 24 is expanded to nearly the diameter of the vessel so that when it is moved to push out an occlusion, it will avoid trauma to the wall of the vessel. Further, the membrane on the expanding element will aid in decreasing the trauma to native vessels as described above. In such a case, the engaging element (and the blocking element) may be used only as a seal so that the obstruction may be removed or otherwise obliterated. This seal allows the rest of the vessel to be uncontaminated and provides for a closed system for irrigation and/or aspiration and subsequent obliteration or removal of the obstruction FIG. 4 illustrates the catheter 16 with the malecot 18 in an expanded state on the distal end of the catheter. A membrane 20 is normally used in order to provide a complete blocking or sealing function. Further, the membrane 20 may aid in locking the blocking element in a particular shape. This malecot type element is created by making longitudinal slits in the sidewall of the catheter (or an attachment bonded thereto) thereby creating links or wings that will expand when the distal end of the catheter is pushed in a proximal direction. The appropriate pushing of the proximal end of the catheter is achieved, as shown in FIG. 5, by a ferrule 30 which is a standard tip on a standard dilator 28. Alternatively, the dilator 28 may be a guide wire (which is usually much longer and flexible than a dilator) for remote obstruction removal. In such an application of the present invention, the guide wire would have a ferrule type mechanism that would act like the ferrule on the dilator. In this instance, the guide wire (with ferrule) would be inserted into the vessel to the obstruction. The catheter would then be pushed along the guide wire until it reached the ferrule which would normally be located near the distal end of the guide wire. At this point the wire would be pulled back, the ferrule would butt against the catheter and force out the blocking sealing element. The engaging element may be used with this blocking element and it could even be the ferruled wire as well.

It should be noted that the retention catheter described in U.S. Pat. No. 3,799,172 issued on Mar. 26, 1974 to Roman Szpur illustrates a structure that is similar to the malecot type device 18 illustrated in FIG. 4; although in that patent it is used as a retention device whereas here it is used as a blocking element.

This blocking element 18 is often called a malecot in the industry. It should be understood herein that the term malecot is used to refer in general to this type of multi-wing device.

Figure 6:
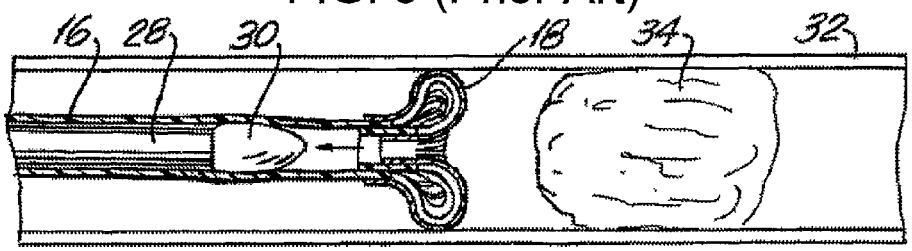

More specifically, as shown in FIG. 5, the catheter 16 together with a dilator 28 having an expanded tip 30 which is a ferrule is inserted into a vessel 32 such as the graft shown in FIG. 1. The catheter 16 and dilator 28 are inserted close to the occlusion 34 and then the dilator 28 is removed. Proximal motion of the dilator 28 causes the tip 30 to contact the distal end of the catheter 16 forcing the distal end of the catheter to put pressure on the malecot wings creating the expansion shown in FIG. 6 (and also schematically shown in FIG. 1). Once this expansion has occurred, the dilator with its tip can be removed from the catheter (as shown in FIG. 6).

Figure 7:
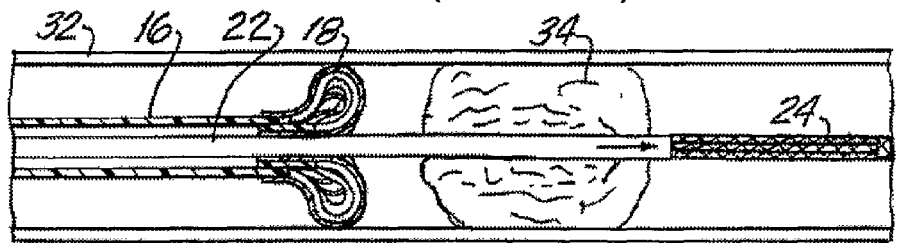
Figure 8:
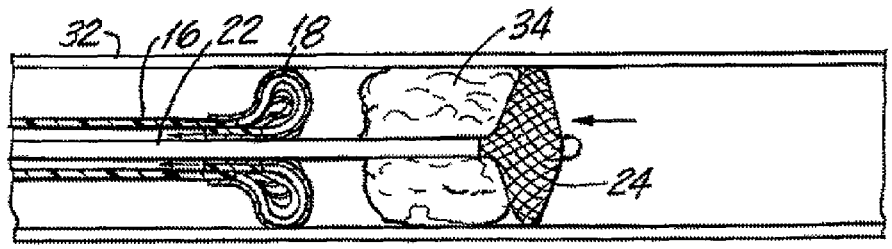

What then occurs is shown in FIGS. 7 and 8. As shown in FIG. 7, the support wire 22 with its braided removal element 24 is inserted in the collapsed state so that it passes through or around the occlusion 34. It should be noted that the support wire 24 may be inserted prior to the blocking catheter being inserted or after the catheter is inserted (the latter of which is illustrated in the FIGS.). Most of the occlusions to which the device of FIGS. 1-8 is directed, such as congealed blood in a graft, will permit a support wire 22 to pass through it because the consistency is that of viscous material which can be readily penetrated. Alternatively, if the occlusion is a non viscous material such as a stone, plaque, emboli, foreign body, etc. the support wire 22 is small enough to be passed around the occlusion. Once the braided element 24 is on the distal side of the occlusion 34, the actuator rod 26 is pulled creating the expanded state for the braided device. Accordingly, distal movement of the entire support wire will cause the expanded braided device to move against the occlusion and force it into the catheter for removal with or without aspiration. When removal of obstructions that are located some distance away from the point of access into the body such as the carotid artery via a groin access the wire 22 would likely be inserted first. In this case the support are 22 with its expanding element 24 may be used as a guide wire to guide the catheter to the preferred location. Of further import is that the blocking element and the engaging element may be used without any relative motion once deployed. Such is the case when irrigation and/or aspiration is used for the obstruction removal. In this case the two elements can be used as seals against the tubular inner walls on both sides of the obstruction whereby the obstruction is removed from that sealed space with the use of aspiration, irrigation, or both. Further other means of obliterating the obstruction within this sealed space may be employed. Some of those means are, but are not limited to the addition of dissolving agents, delivery of energy such as ultrasound, laser or light energy, hydraulic energy and the like.

Other Comments

An important consideration of the device described herein is that the support wire with its expanding element can be fabricated with a very small diameter. This is important because it allows an optimally large annular space between the wire and the inside of the catheter for maximum obstruction removal. Previous engaging elements have been used that use a balloon for the engaging element. This balloon design requires a larger shaft diameter than that of the present invention. Hence in these previous devices the annular space is not maximized as in the present invention. The term wire is used to refer to the support portion of the removal device. The material of the wire need not necessarily be metal. Further, it may be desirable to use a 'double' engaging element (i.e. two braided or malecot expanding elements separated a distance appropriate to entrap the occlusion) in the case for example where the occlusion is desired to be trapped in the vessel. The term wire is used herein to refer to a dual element device having a shell component and a core or mandril component which are longitudinally moveable relative to one another so as to be able to place the braided occlusion engaging element into its small diameter insertion state and its large diameter occlusion removal state.

Figure 9:
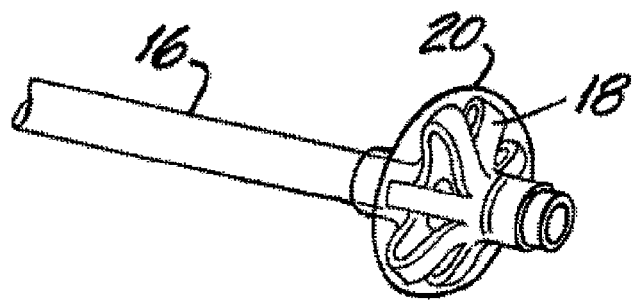
Figure 10:
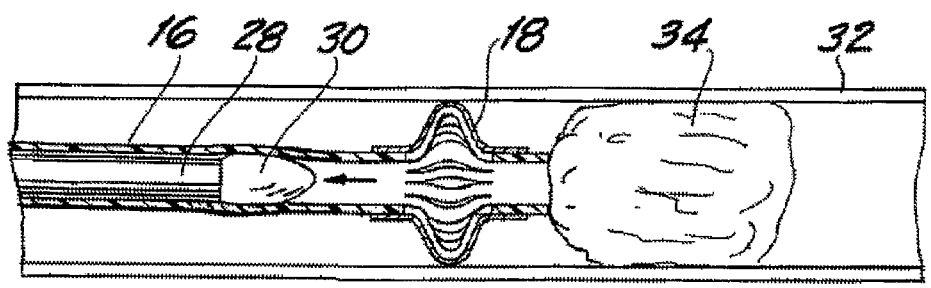

Although the blocking element is described as a malecot type of device, it should be understood that the blocking element may be designed in various fashions which are known in the art. See, for example, FIGS. 9 and 10. As another example, an appropriately designed braid arrangement could be used as the blocking element. In that case, the catheter may have to be a dual wall catheter in which the inner and outer annular walls are able to move relative to one another in a longitudinal direction so as to place the braid used as a blocking element in its small diameter insertion state and its large diameter blocking state. Alternatively, it may be a single wall similar in design to the malecot style blocking element described previously.

It should be further understood that there might be a situation in which the blocking element or even the occlusion engaging element would be provided to the physician in a normal expanded state so that when the device is deployed, it would, through plastic memory or elastic memory, automatically snap into its expanded state.

Discussion of Method for Treating a Target Site in a Vascular Body Channel

The above-described structure and methods provide a good background for the following description of the presently claimed invention. Corresponding structures are referred to with corresponding reference numeral, such as support wire 22/support wire 122, and occlusion 34/occlusion 134.

Figure 11:
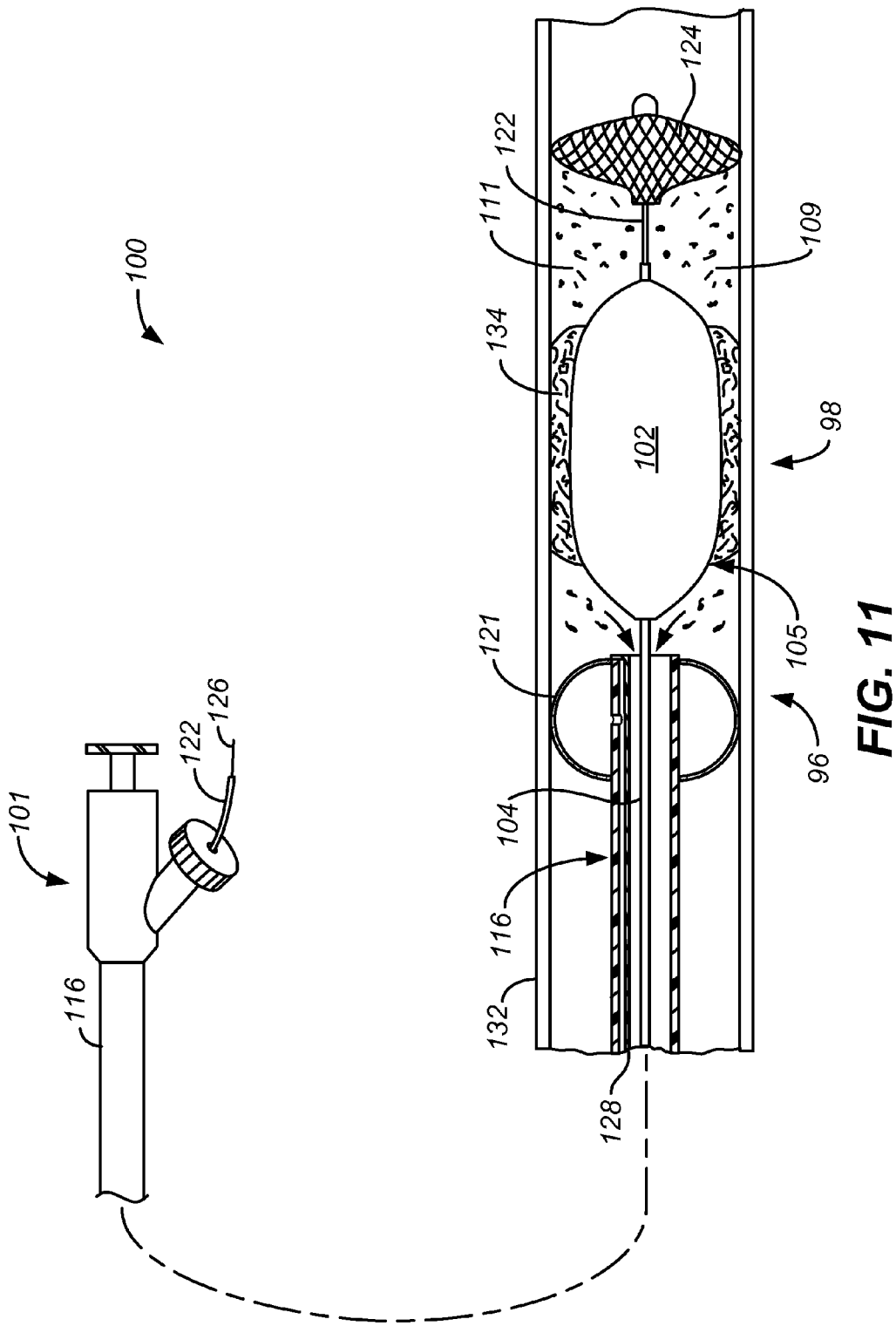
FIGS. 11-20 illustrate examples of the presently claimed invention.

FIG. 11 illustrates a catheter assembly 100 including a proximal end portion 101, from which proximal occluder catheter shaft 116 extends and passes into blood vessel 132, and a distal end portion 96 at a target site 98 within blood vessel 132. Distal occluder 124 is positioned at a location distal of target site 98 while balloon type proximal occluder 121 is positioned at a location proximal of the target site to define a region 109 therebetween. Occluders of types other then those illustrated as proximal and distal occluders 121, 124, such as malecot type occluders, can also be used. However, the annular balloon type of proximal occluder 121 illustrated is presently preferred for its simplicity of construction and lower cost. Catheter assembly 100 also includes a balloon assembly 105 comprising a balloon catheter shaft 104 passing through proximal occluder catheter shaft 116 with a balloon 102 at its distal end. Support wire 122, with an actuator 126 passing therethrough, extends from distal occluder 124 and passes through balloon catheter shaft 104. Balloon 102 is shown in an expanded state pressing against occlusion 134. If desired, balloon 102 could be a drug eluting balloon. FIG. 11 also shows an injected agent 111 within region 109. Agent 111 may include various types of therapeutic and/or diagnostic agents, such as paclitaxel, sirolimus, other anti-proliferative drugs, contrast agent, thrombolytic agent, agents to dissolve the obstruction, agents to change a vulnerable plaque to a non vulnerable plaque and the like. As discussed in more detail below, agent 111 acts on the occlusion 134 and the inside surface of a vessel 132 at the target site 98 during the intervention, in this example by balloon 102.

Figure 12:
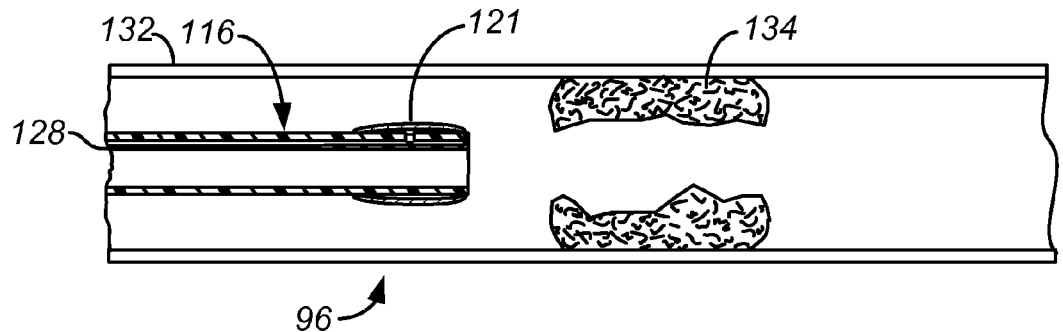
Figure 13:
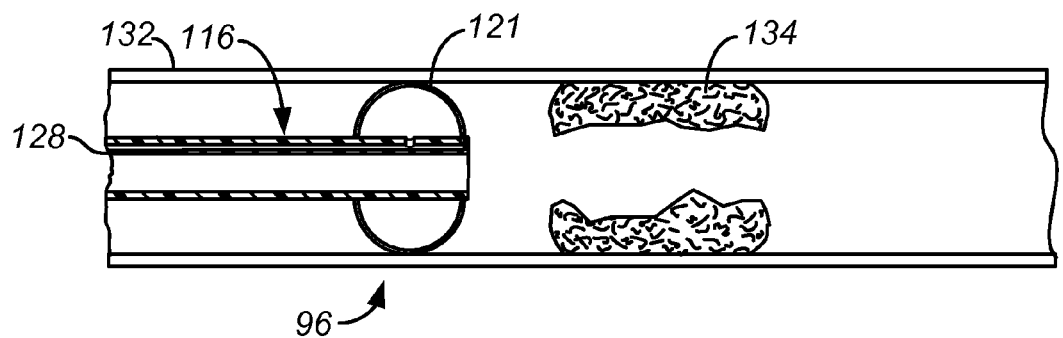
Figure 14:
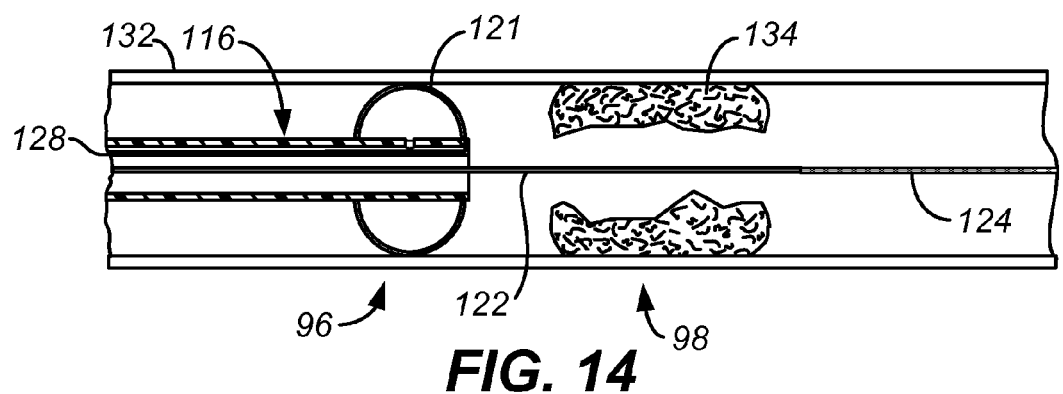
Figure 15:
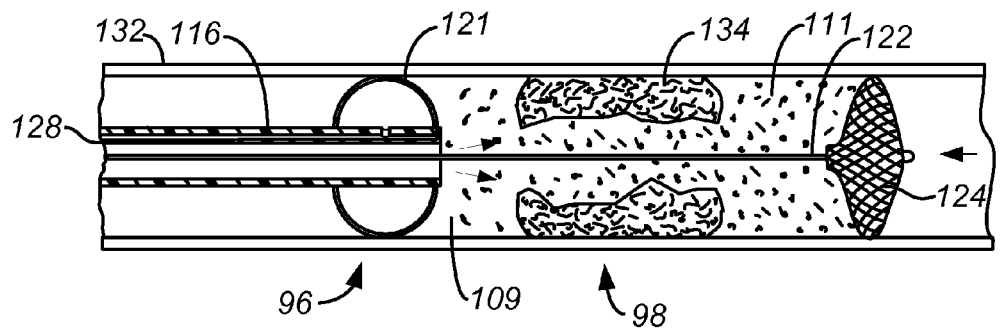
Figure 16:
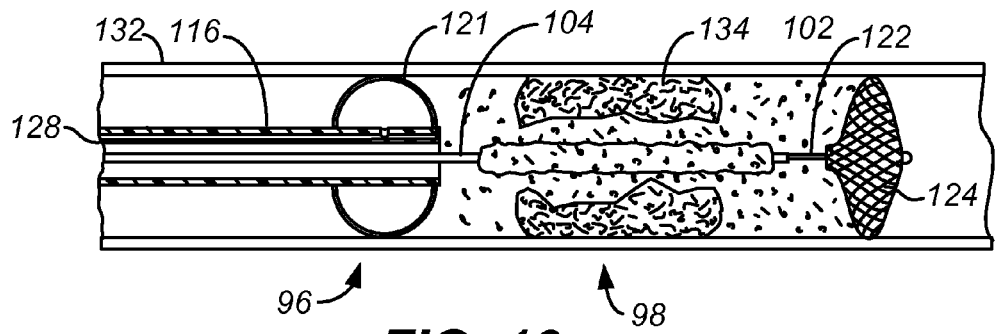
Figure 17:
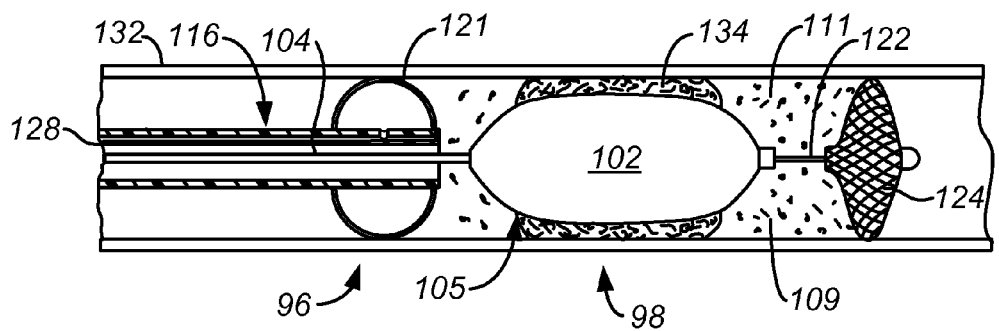

FIGS. 12-14 show the initial steps during the use of catheter assembly 100. These steps correspond to FIGS. 5-7, discussed above, with the exception that occlusion 134 does not totally block blood vessel 132, and therefore will not be described again. FIG. 15 is similar to FIG. 8 but also shows the introduction of injected agent 111 into region 109 between proximal occluder 121 and support wire 122. In some examples region 109 is aspirated through catheter shaft 116 prior to injecting agent 111. The use of proximal and distal occluders 121, 124 concentrate agent 111 at and around occlusion 134 at target site 98. FIG. 16 shows balloon catheter shaft 104, with a balloon 102 at its distal end, inserted over support wire 122 until balloon 102, in its deflated state, is positioned at occlusion 134. FIG. 17 shows balloon 102 expanded against occlusion 134. Balloon 102 is then deflated, back to the state of FIG. 16, followed by the removal of balloon assembly 105 to the condition of FIG. 15. Region 109 is then aspirated to remove material from the region; the aspiration may be in conjunction with pulling distal occluder 124 proximally at least part of the way towards proximal occluder 121 and/or partial collapse of distal occluder 124 to permit retrograde blood flow past the distal occluder 124 and into region 109. Alternatively the contents of region 109 may be allowed to flow downstream as the total dose administered would likely not be harmful to the patient. After aspiration of region 109 is complete, distal occluder 124 is collapsed to the condition of FIG. 14 and pulled back into catheter shaft 116. Proximal occluder 121 is collapsed by deflating balloon 102 through balloon catheter shaft 104.

The entire time balloon 102 is operating on occlusion 134, or some other intervention is being conducted at the target site 98, agent 111 is present to bathe target site 98, including occlusion 134 and the inner wall of blood vessel 132 between occluders 121 and 124. This aspect of the invention is extremely important because both the intervention, such as with angioplasty balloon 102, and the injected agent therapy are conducted essentially simultaneously without the need for removal and replacement of catheters and interventional tools.

In some examples proximal and distal occluders 121, and 124 are maintained in place to maintain agent 111 at target site 98 for a period of time, such as several minutes to hours, after balloon 102 has been collapsed. In some situations more than one target site 98 may be treated through the placement of occluders 121, 124 in contracted states, moving the occluders to a new target site, re-expanding the occluders to their expanded states followed by injecting a agent 111 into the newly created region 109 and performing an intervention at the target site, typically using a balloon 102.

Ever since stents were introduced in the 1980's, investigators have searched for devices and methods to provide temporary support to the vascular wall without leaving a stent, which can never be removed, in the vessel forever. Bare metal stents have an unacceptable restenosis rates, and drug eluting stents, while having a moderately acceptable restenosis rate, are extremely expensive, have long term sequelae such as late stent thrombosis, and patients must stay on costly and potentially dangerous platelet inhibitor and other drugs for one year to life. Biodegradable and bioabsorbable stents have been proposed and produced, but they are less effective than either bare metal stents or drug eluting stents.

One particular use of this device, which is mentioned elsewhere, is to utilize part or all of the system before a bare metal stent (BMS) delivery. Drug eluting stents (DES) deliver the drug to only a small portion of the vessel wall that is stented because of the spaces between the drug eluting stent struts. Utilizing the current device with the agent injected into the closed space 109 before expansion of a BMS would bathe 100% of the vessel wall and still have the stent present to counteract elastic recoil, if it did occur, remodeling of the vessel, dissections, and other problems associated with vascular interventions. The BMS could be used with the proximal and distal occluders primarily. Alternatively, the temporary balloon stent apparatus could be utilized with the occluders and the agent between them as outlined below. If there was an unsatisfactory result after treatment with the entire system of occluders, agent, and temporary balloon stent, then the BMS may be deployed as a "bail-out" procedure. The agent may or may not be reapplied, having already been utilized before the aforementioned temporary stent application.

The prior art does not address a removable balloon stent apparatus that dilates the plaque and supports the wall after plaque dilatation. Lashinski et al. in U.S. Pat. No. 6,773,519 describe a stent like device which is deployed and then removed, and describes a removable coupler which is part of the device, but not a removable stent. Tsugita in U.S. Pat. No. 6,652,505 describes a guided filter which may be used to deliver a stent and removed, but not a removable stent. Kahmann in U.S. Pat. No. 5,879,380 describes a device and method for relining a section of blood vessel that has been injured or removed, not a device to both dilate the lesion and prevent elastic recoil as does the example of the present invention discussed below with reference to FIGS. 18-20.

Figure 18:
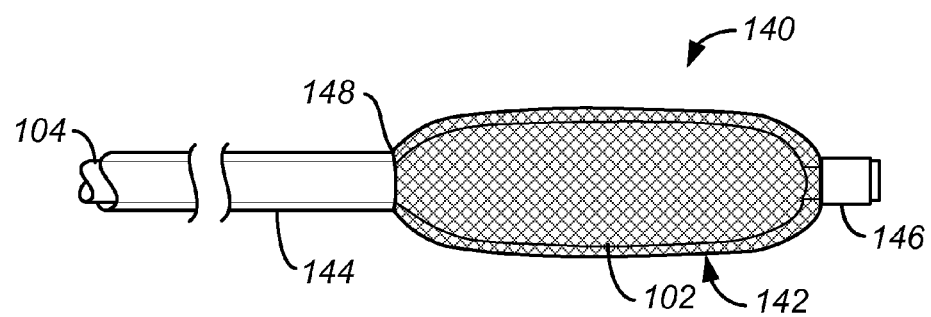

A further example of the invention will be described with reference to FIGS. 18-20. This example is intended to dilate the occlusion 130 and inhibit elastic recoil by providing temporary stenting. Balloon assembly 140 includes balloon catheter shaft 104 with balloon 102 at its distal end and an actuator sleeve 144 surrounding balloon catheter shaft 104. A radially expandable braid 142 is positioned over balloon 102. Balloon 102 and braid 142 are shown expanded in FIG. 18. The distal end 146 of braid 142 is secured to the distal end of balloon catheter shaft 104 while the proximal end 148 of braid 142 is secured to the distal end of actuator sleeve 144. Therefore, braid 142, although a stent like structure, is a nonremovable part of balloon assembly 140 and is removed from the patient following the procedure.

Figure 19:
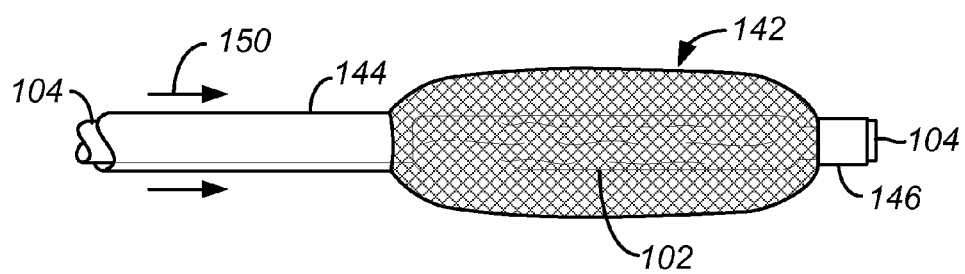

FIG. 19 shows balloon 102 and a collapsed state and that by moving the actuator sleeve 144 distally in the direction of arrows 150, the braid 142 will become expanded over the collapsed balloon 1, as shown in FIG. 19, and will stay expanded when balloon 102 is deflated and collapsed. The braid 142 is fixed to the catheter shaft 104 distally, but not to the balloon 102. It is in this expanded state of braid 142 and collapsed state of balloon 102 that the braid will act as a stent like structure and allow blood flow to be restored.

Figure 20:
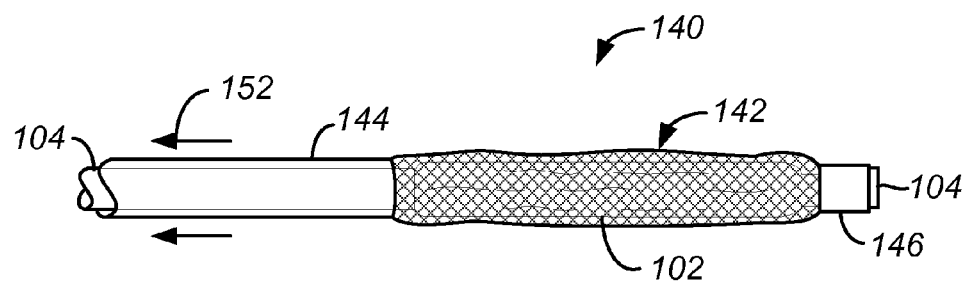

In FIG. 20, by moving the actuator sleeve and 44 proximally in the direction of arrows 152, the braid 142 will be contracted against the deflated and collapsed balloon 102, and may even help lower the profile of the collapsed balloon. It is in this contracted state that balloon assembly 140 is inserted and removed.

Balloon assembly 140 can be used by itself, that is not as a replacement for balloon assembly 105 of catheter assembly 100 of FIG. 11. However, by using balloon assembly 140 as a part of catheter assembly 100 additional advantages are achieved. Four separate but complementary actions are achieved relative to the inside surface of blood vessel 132 and occlusion 134: 1) It provides a time proven balloon action to effectively dilate the occlusion, 2) It provides a mesh braid over the balloon to more evenly apply stresses on the plaque and thus cause less dissection and injury, 3) The braid, acting independently of the balloon, acts as a transient, removable stent to lessen acute elastic recoil, and 4) When combined with a drug delivery, it will inhibit restenosis. Currently, there are several companies in various stages of development and commercialization of drug eluting balloons. However, these devices do not possess the mechanical advantages of the present invention, i.e., the braid to create crevices that allow the plaque to be more homogeneously compressed at lower pressures with less injury, and the ability of the braid to be used as a transient, temporary, or removable stent to reduce the incidence of acute elastic recoil, and acting in concert with the agent to prevent restenosis.

Because the braid 142 is not attached to the balloon surface, it acts independently of the balloon 102. It is normally expanded with the balloon, but when the balloon is contracted or collapsed to allow for distal blood flow to recommence, the braid can be locked into an expanded configuration by manipulating catheter shaft 104 and actuator sleeve 144 with one's fingers. It is proposed that by leaving the braid expanded for several minutes while blood flow is restored distally, the smooth muscle will accommodate the stretch of the angioplasty. This may well diminish the incidence of acute elastic recoil, one of the major acute problems of POBA. In fact, it is known that prolonged expansion of the vessel has just this effect; however the time that a balloon can be left expanded is limited as ischemia will develop.

The sum of these advantages, i.e., the mechanical advantages of the braid in dilating the plaque with less pressure, less dissection, and less injury along with the temporary stent usage further combined with drug elution to inhibit restenosis is expected to significantly improve patient outcomes.

The present invention has the potential to dramatically improve the results of POBA and the potential to improve the results of and replace DES in many cases, especially due to the ability to block the effects of recoil. Such cases include patients with in-stent restenosis, bifurcation lesions, and small vessels lesions. DES will likely remain a dominant strategy in treating many lesions and there will always be a need for stenting, atherectomy and other complex treatments; but clearly if feasibility is shown and the present invention lives up to its expectations, the present invention could become the treatment of choice for most angioplasty procedures. In those cases in which it may not achieve optimal results, BMS (or even DES) may then be utilized.

The present invention occludes the lumen with a device that will allow the angioplasty catheter shaft 104 to pass through it, and by occluding the distal aspect of the vascular channel to be perfused with the agent, the angioplasty balloon 102 and/or stent delivery balloon assembly 140 may be placed through the proximal occluder catheter shaft 116 and over the support wire 122 of the distal occluder device, the drug infused and the angioplasty and/or stent delivery can take place while the drug is present. This will allow the pressure of the angioplasty balloon 102 and/or stent delivery balloon assembly 140 to force the drug into the vessel wall while the plaque/vessel is being dilated. The drug would be delivered during the procedure and before platelet adhesion would prevent some of the drug from accessing the vessel wall as in the case of existing prior art. The presence of the drug while the action on the plaque or vessel is taking place will certainly deliver more drug to the vessel wall than just passively bathing the vessel after the intervention.

The procedure could take several forms but one method would be to perform an angiogram to identify the lesion to be treated at the target site 98. After the lesion is identified, advance a diagnostic catheter beyond the occlusion 134 and deploy the distal occluder 124, which is support wire 122 and pull wire 123 based. Distal occluder 124 is essentially a mesh braid covered with an impermeable substance. The diagnostic catheter is removed and the proximal occluder catheter shaft 116, with proximal occluder 121 at its distal end, is inserted over the guide wire/distal occluder and the tip of the proximal occluder is positioned proximal to the lesion. The proximal occluder could be balloon based or non balloon based. Balloon based occluders are common in prior art. There is a mesh braid funnel catheter occluder invented by the current inventor which occluders without the use of a balloon; see U.S. Pat. No. 6,221,006, the disclosure of which is incorporated by reference. The proximal occluder 121 and then the distal occluder 124 would be activated so that compete occlusion of the vascular lumen would be achieved. The blood would be aspirated from the region 109 between the proximal and distal occluders. The agent would be injected as injected agent 111. The agent and its concentration would be determined by the physician. The agent usually would be mixed with contrast so that it would be visible under fluoroscopy. The angioplasty balloon assembly 105 or the stent delivery balloon assembly 140 device or a stent delivery device (not shown) with a BMS or DES would be placed over the support wire 122 of the distal occluder 124 and centered on occlusion 134. The angioplasty or stent delivery would then be performed within this closed system with the agent in place. The angioplasty balloon assembly 105 or stent delivery balloon assembly 140 could then be removed through the proximal occluder 121, and the agent aspirated. The distal occluder 124 would be released and further aspiration done until blood was returned insuring that all of the drug had been aspirated before releasing the proximal occluder. The proximal occluder 121 would then be released, restoring blood flow distally.

Alternatively at this point of the procedure, if a second dilatation was desired, the drug could be aspirated through the proximal occluder after the initial dilatation similar to the above procedure, but before the angioplasty balloon was removed. Similar to above, the distal occluder would be released first while still aspirating. After blood was returned in the aspiration fluid, assuring that the entire amount of drug had been aspirated, the proximal occluder would be released restoring blood flow distally. A second dilatation of the angioplasty balloon could then be performed in a standard conventional manner without any drug being present, the drug having been delivered during the first dilatation.

However, if the desire was to deliver drug during the second dilatation, then the procedure above for the first dilatation could be repeated in a slightly modified manner. There would usually be no need to remove the angioplasty balloon. The proximal occluder would be activated, followed by the distal occluder. The blood aspirated and the drug injected through the lumen of the proximal occluder, and around the shaft of the angioplasty balloon. Then the second angioplasty dilatation could take place, the drug aspirated, the distal occluder released during aspiration, and the proximal occluder released to restore blood flow.

If two separate lesions in the same vascular region needed to be treated, the above may be modified somewhat. After the first lesion was treated as above, the occluders, balloon and temporary balloon stent would be collapsed and moved to a second location where the procedure would be repeated without the laborious step of changing catheters and so on. This would save time and cost, as most balloon catheters cannot be withdrawn and then reinserted into the body as the balloon folds cause reinsertion to be difficult and impractical.

If balloon assembly 140 were utilized in the above procedure instead of a conventional angioplasty balloon, braid 142, acting as a temporary stent, could remain expanded against the vessel wall in a stent like manner during the first balloon inflation, between inflations, during the second balloon inflations and for a chosen period after the last balloon inflation. This action would not only effectively deliver the drug to the vessel wall, but also would provide a temporary stenting effect to the vessel wall to inhibit acute elastic recoil.

Moreover, if balloon assembly 140 were utilized it would provide less injury to the vessel wall by dilating the occlusion at lesser pressures and causing fewer dissections. Therefore, the essence of this procedure is to create less damage to the vessel wall, prevent elastic recoil, compress the plaque efficiently, and to deliver a drug to inhibit intimal hyperplasia as a cause of restenosis.

This procedure has many different ways of being performed as a standard angioplasty balloon, such as balloon 102, may be used, a specialty device, such as a balloon assembly 140, may be used; in addition, stent delivery devices, laser devices, cryoplasty and most any device designed for endovascular treatment of vascular disease may be used in accordance with the present invention. The present invention device differs from prior art in that a non-balloon distal occluder is preferably used in the procedure. This one step makes it possible to perform the drug perfusion and the intervention in a single step vs. the cumbersome method of having to exchange catheters and then deliver the drug after the fact, or at least after the intervention. While other components of this device have been invented for the purpose of perfusing drug after angioplasty, the presence of a guide wire (support wire 122) occluder, with any type of proximal occluder that could be traversed by a catheter, makes this device a superior one as it allows the intervention to be performed while the lesion and vessel wall are being bathed by the drug or other agent. Of course a balloon occluder could be used distally in the method described above if it contained a shaft thin enough for an inflation channel and means to allow insertion of a treatment device coaxially over the distal occluder shaft, and it is included by this mention as an alternative embodiment.

The one feature of the ability to place the treatment device over the shaft of the distal occluder so that the treatment is conducted concurrently with the drug delivery is important to the commercial success of the procedure and method of infusing a drug to inhibit restenosis as it obviates the less than effective method of delivering the drug in a second step in an inefficient manner after the intervention, and with a good deal of pressure upon the vessel wall. Therefore, an aspect of the invention relates to performing the interventional procedure while the agent is contained within the vascular space. The present invention will permit treatment of variable lengths of vessel with the one device vs. the fixed lengths of devices for treating vessels in prior art. If an arterial segment that is stenosed is for example, 1.0 or 2.5 cm in length, then the entire occlusion 134 can typically be treated with a single placement of proximal and distal occluders 121, 124. If the lesion is 25 cm or 50 cm or 100 cm in length, then the same device can be used to treat any of those lesions by varying the length between the proximal occluder and the distal occluder to treat the desired length as the proximal and distal occluders are not connected by a fixed distance as in the prior art. In long lesions, the prior art devices would need to successively move the fixed distance proximal and distal occluders (usually balloons) and provide short overlaps between each segment for multiple segments and multiple treatment sessions. The method of the current invention would save time, obviate repeated repositioning of the prior art device and obviate the use of multiple doses of the drug or other substance.

Balloon assembly 140 is inserted into blood vessel 132, positioned at occlusion 134, and the balloon 102 inflated in a standard manner. The inflation of the balloon will expand the braid 142 and this is the usual method of expansion of the braid. More importantly is that the lesion will be dilated successfully, probably with a lesser pressure than a conventional POBA balloon. See FIG. 18. After a first length of time chosen by the operator, typically one or two minutes, the balloon is deflated while force is exerted on the actuator sleeve in the direction of arrows 150. See FIG. 19. This keeps the braid 142 expanded against the vessel wall while the balloon 102 is contracted allowing for blood flow to be restored distally for a second length of time, usually more than 3 minutes and typically 3 to 90 minutes. The proximal occluder and of the distal occluder are collapsed after the balloon is deflated to restore flow in the vessel while the braid is expanded against the vessel wall. The balloon inflation may be repeated as many times as desired, and by keeping forward force on the actuator sleeve 144, the braid 142 will remain expanded during, between, and after balloon inflations. There may be a locking mechanism provided so that the forward force is maintained without manual pressure. Moreover, the temporary stent may be used with modalities other than drugs, such as radiofrequency, electroporation, heat, atherectomy, gene therapy, cryotherapy, electrical currents, radiation, iontophoresis, other pharmacological agents and substances, and the like.

Combining the elements of the current invention, including the temporary stent to dilate the lesion at a lesser pressure with less injury to the wall and to be utilized to reduce or eliminate elastic recoil along with one or more of the other modalities, may eliminate the need for the administration of a drug agent to inhibit restenosis. However, combining the drug administration with another modality listed above and the temporary stent element may even further solve many of the short and long term sequelae of vascular intervention, and may even further eliminate the need for stenting or surgery in many cases. If the dilatation of the lesion was adequate because of the proven effect of the typically wire-like temporary stent exterior to the balloon being able to dilate plaque more effectively than POBA, if the lesion was held open by the temporary stent while the drug acts upon the smooth muscle cells and to relax them preventing elastic recoil, and another modality from the list above, for example electroporation, was utilized to enhance the absorption of the drug and to act on the cells of the vascular wall independently to further inhibit restenosis, then all of the reasons to use conventional, non-temporary stents would be obviated. The problems that stents solve would be eliminated. There would be no reason to use a stent in many cases, and this would benefit the patient and the healthcare system. Stents are not only costly, but have long term negative consequences, including in-stent restenosis, late stent thrombosis, and the need to be placed on expensive and potentially deleterious drugs for extended periods.

Figure 21:
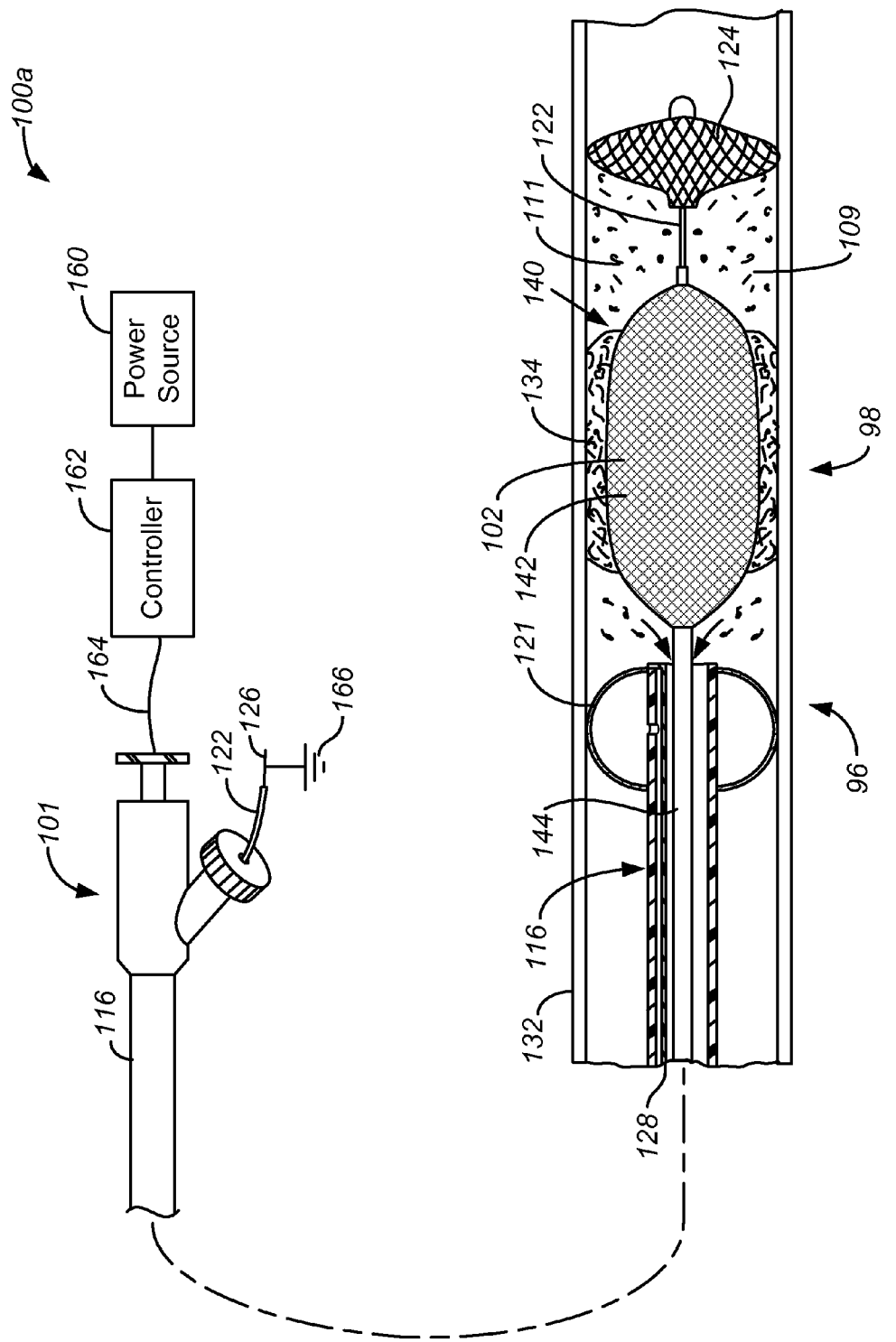
FIG. 21 illustrates an electroporation catheter assembly similar to the examples of FIGS. 11 and 18.

In the case of electroporation, and some of the other modalities, an electrically conductive temporary stent could be use to transfer the energy or electrical pulses to the vessel wall. FIG. 21 illustrates an electroporation catheter assembly 100a constructed to permit the application of electric current to the wall of blood vessel 132 to create transient pores in the cell membrane through which, for example, a drug may pass. Braid 142, acting as a temporary stent, is connected to an external power source 160 and a computer-based controller 162 by wires 164 within the wall of external actuator sleeve 144. Controller 162 would be utilized to program the pulse duration, sequence, amplitude, voltage, amperage, and other parameters to deliver the prescribed energy or electrical pulses to the vessel wall through the temporary stent. It may also be utilized to ascertain electrical impedance or other feedback parameters so that the proper energy parameters may be programmed or prescribed. In this example actuator 126 electrically connects distal occluder 124 to ground 166 thereby grounding the vessel wall. Alternatively, the energy, such as in the form of electrical pulses, may be delivered through a configuration other than the temporary stent. The electroporation may be used to facilitate the delivery of a drug, but also may be used alone to create the pores in the wall of the cell without the drug being present. The cell is then unable to recover from having these pores in the wall, and it eventually dies, in effect a type of accelerated apoptosis. Adding the additional modality to the system of occlusion elements, drug infusion, dilatation and temporary stenting described herein would add very little incremental cost, but may be necessary to reduce the restenosis rate under the 10% rate expected from the above system without the additional modality.

The medical literature demonstrates that paclitaxel acts on the cytoskeleton or microtubules within smooth muscle cells by enhancing polymerization and causes the smooth muscle cells to relax. There are other cellular effects, certainly, but the dysfunctional microtubules are thought to be reason the smooth muscle cell relaxes rather than contracts as a result to exposure to certain drugs. The temporary stent created by braid 142 combined with paclitaxel should provide enough time of prolonged distension of the vessel for the paclitaxel to act upon the cytoskeleton and microtubules so that the smooth muscle cells would not contract upon the removal of the temporary stent. The present invention can take advantage of paclitaxel or other antiproliferative drug through the use of the braid 142 acting as a temporary stent to provide this action of prolonged expansion, allowing the drug to act upon the cells so that they will not contract when the temporary stent is removed. Without the prolonged expansion, the drug would likely not have enough time to act upon the cellular components to cause the smooth muscle cell to relax. The extra time provided by the expanded temporary stent while blood is flowing through the area along with the uptake and action of the drug will likely result in diminished elastic recoil of the vessel, and better long term patency.

The present invention also provides a method of infusing an antiproliferative drug or other agent that acts upon the smooth muscle cells and structures within the arterial wall and prolonging the distension of the vessel with a balloon, a temporary stent or scaffolding, or other structure to reduce the incidence of elastic recoil, restenosis, and/or other effects of the intervention.

In one example the above method would entail placing the proximal and distal occluders on each side of the lesion to create an isolated region, activating the proximal and distal occluders, injecting the drug, performing the therapeutic angioplasty intervention with a temporary stent device as has been described leaving the temporary stent expanded against the vessel wall, deflating the angioplasty balloon so blood flow could be restored subsequently, aspirating the drug along with other flowable material (or even removing it from the isolated region by releasing it downstream), deactivating the proximal and distal occluders, and removing the distal occluder. This would restore flow in the vessel, but the temporary stent would still maintain annular pressure against the vessel wall to prevent elastic recoil while the drug, having been absorbed by the smooth muscle cells, acts upon the microtubules of those smooth muscle cells to create a relaxation of these smooth muscle cells and prevent acute elastic recoil. In some examples the drug or other agent is allowed to contact the target site for a period of time, such as from 30 seconds to 20 minutes, before the therapeutic angioplasty intervention, or other pressure applying step, is performed. In some examples the angioplasty balloon, or other pressure applying apparatus, is used to apply pressure to the vessel wall from about one minute to five days. When the balloon is left in place for extended periods, it is usually in a collapsed state to permit blood flow around it. It is expanded only when necessary, such as to expand the lesion during angioplasty and to expand the temporary stent.

Alternatively, the above example may be modified so that instead of a temporary stent, a plain angioplasty balloon device, a stent, such as a bare metal stent or a bioresorbable or biodegradable stent which is intended not to be removed, atherectomy, or other therapeutic device is utilized. Also, the deactivated proximal and distal occluders may be left in place within the vessel while a pressure device is providing force against the vessel wall, and removed when the pressure device is removed. The temporary stent or other pressure device would typically remain in place for at least several minutes and at most for several hours to days to prevent elastic recoil. If, for example, the balloon assembly 140 of FIG. 20 is left in place for several days, balloon 102 is collapsed permit blood flow around it. In such a procedure heparin or some other agent could also be administered.

Moreover, the temporary stent may be used with other modalities other than drugs, such as radiofrequency, electroporation, heat, atherectomy, gene therapy, cryotherapy, electrical currents, radiation, iontophoresis, other pharmacological agents and substances, and the like.

Other variations of temporary stenting, can be used. For example, the braid 142 may be contracted by guide wire(s) instead of the actuator sleeve 144. The braid may be contracted by moving the distal part of the braid more distally by using an engagement device instead of an actuator sheath. In other words, if the distal aspect of the braid was engaged or attached to the distal aspect of the guide wire rather than fixed to the distal aspect of the balloon catheter as described in the preferred embodiments, then moving the guide wire distally would collapse the braid and moving the guide wire proximally would expand the braid, or at least maintain expansive pressure upon the already expanded braid.

The current invention differs significantly from the Ya patent discussed above in that the present invention uses no dissolving agent outflow bores, is not directed to dissolving a thrombus, and any antiproliferative agent is injected before the intervention and is present during the therapeutic intervention, not removed before the intervention as in Ya. Any subsequent intervention or therapy (angioplasty, stent placement, and the like) are performed after the removal of the dissolved thrombus in Ya. Moreover, the thrombus dissolving agent and the dissolved thrombus must be removed in the method of Ya, which is aimed at removing a thrombus, whereas there is typically no need to remove any antiproliferative agent when practicing the present invention. The dose of the antiproliferative agent is much lower than the systemic dose administered a patient receiving chemotherapy for treatment of a tumor.

In most embodiments disclosed in the Zadno-Azizi reference discussed above, the device is comprised of two distinct lumens, an irrigation pathway and an aspiration pathway, much different from the device and method of the current invention. In the single example disclosed in Zadno-Azizi in which there is only a single aspiration path, the therapy catheter must be removed for the device to function. In contrast with the present invention it is preferable to leave the therapy device in place even if the injected substance is to be removed. In many cases, there is no need to remove any antiproliferative agent used with the present invention, again a distinction from the method of Zadno-Azizi. The fluid containing the embolic material must be withdrawn for the Zadno-Azizi to be effective less the embolic material embolizes downstream. The success of the present invention is not predicated on removal of any injected drug, as the drug may be released downstream where it likely would be harmless to the tissues.

Even more important in differentiating the present invention from the method of Zadno-Azizi is the timing aspect. The fluid injected and aspirated is done after the therapeutic invention with the Zadno-Azizi method whereas the present invention using an agent to inhibit restenosis, such as, but not limited to paclitaxel, the agent is injected before the therapeutic procedure and left in place during the therapeutic procedure. The antiproliferative agent may or may not be aspirated subsequent to the therapeutic procedure.

Moreover, the prior art devices of Ya and Zadno-Azizi both use a distal occluder with a hollow lumen, which is needed to inflate the distal balloon. The present invention has no need for this feature when the distal occluder is a mechanical blocking element so that they are in no need for a hollow lumen along the distal occluder.

The balloon stent assembly of the current invention, in contrast with known the temporary stents, will both dilate the plaque in a controlled manner using the balloon, which causes little injury to the vessel, and supports the vessel for an extended period of time using the temporary stent. Known temporary stents are commonly intended to only support the vessel after something untoward happens during the procedure, i.e., dissection, vasospasm, or vasoconstriction. The current invention, because all of the functions (dilatation and support functions) happen more or less simultaneously, prevents noticeable dissections, vasospasm, or vasoconstriction as the vessel wall is supported during and immediately after the intervention, a great improvement over the prior art device. There is virtually no time for the untoward events to occur with the current invention as there is no time that the vessel wall does not have radial force being exerted upon it. Moreover, the current invention will prevent acute elastic recoil which may be due to many other factors other than dissection, vasospasm, or vasoconstriction.

The above descriptions may have used terms above, below, top, bottom, over, under, et cetera. These terms may be used in the description and claims to aid understanding of the invention and not used in a limiting sense.

While the present invention is disclosed by reference to the preferred embodiments and examples detailed above, it is to be understood that these examples are intended in an illustrative rather than in a limiting sense. It is contemplated that modifications and combinations will occur to those skilled in the art, which modifications and combinations will be within the spirit of the invention and the scope of the following claims.

Any and all patents, patent applications and printed publications referred to above are incorporated by reference.

What is claimed is:

1. A method of treating a target site within a vascular channel of the body using a catheter assembly, the catheter assembly comprising (1) a proximal occluder having an inner lumen and an occlusion element at its distal end and (2) a distal occluder comprising a wire having an occlusion element at a distal end of the wire, the method comprising:

positioning the proximal occluder in a vascular channel-occluding state within the vascular channel with its occlusion element at a first position proximal of a target site thereby occluding the vascular channel at the first position, the vascular channel having an inner wall;

advancing the distal occluder through the lumen of the proximal occluder to position the occlusion element of the distal occluder in a vascular channel-occluding state within the vascular channel at a second position distal of the target site thereby occluding the vascular channel at the second position and thereby defining a region between the distal and proximal occluders;

injecting an agent into the region;

advancing an interventional catheter over the wire of the distal occluder to position an interventional element between the two occlusion elements, the interventional element comprising a stent structure configured to support and maintain pressure against the inner wall and an expandable balloon located within the stent structure;

performing an intervention at the target site with the interventional element while the occlusion elements of the distal and proximal occluders are in their vascular channel-occluding states and the agent is in the region, wherein performing the intervention comprises:
  (i) expanding the balloon to expand the stent structure against the inner wall of the vascular channel,
  (ii) collapsing the balloon leaving the stent structure expanded against the inner wall to maintain pressure against the inner wall,
  (iii) leaving the stent structure expanded against the inner wall for a period of time to inhibit elastic recoil of the inner wall while the balloon is collapsed to allow the occluded region to be bathed by the injected agent through the stent structure, and
  (iv) collapsing the stent structure; and removing the interventional catheter, including the collapsed balloon and the collapsed stent structure of the interventional element, and the catheter assembly from the vascular channel.

2. The method according to claim 1, further comprising aspirating the region prior to injecting the agent into the region.

3. The method according to claim 1, wherein the agent injecting step comprises injecting at least one of a diagnostic agent and a therapeutic agent.

4. The method according to claim 1, wherein said intervention performing step comprises application of electric current to the inner wall of the vascular channel, whereby pores may be created in cell membranes of the inner wall.

5. The method according to claim 1, wherein said intervention performing step comprises application of electric current to the inner wall of the vascular channel through the temporary stent structure, whereby transient pores may be created in cell membranes of the inner wall.

6. The method according to claim 1, wherein the expanding step comprises expanding the balloon against an occlusion on the inner wall.

7. The method according to claim 1, wherein the stent structure is left expanded against the inner wall for longer than 3 minutes.

8. The method according to claim 1, wherein the stent structure is left expanded against the inner wall for 3 to 90 minutes.

9. The method according to claim 1, wherein the stent structure is left expanded against the inner wall for more than 90 minutes.

10. The method according to claim 1, wherein the intervention performing step carried out before the agent injecting step.

11. The method according to claim 1, wherein the intervention performing step comprises performing a first intervention procedure, followed by the agent injecting step, followed by a second intervention procedure.

12. The method according to claim 11, wherein the first and second intervention procedures are substantially the same.

13. The method according to claim 1, further comprising selectively repositioning at least one of the distal and proximal occluders during the intervention performing step.

14. A method of treating a target site within a vascular channel of the body using a catheter assembly, the catheter assembly comprising (1) a proximal occluder having an inner lumen and an occlusion element at its distal end and (2) a distal occluder comprising a wire having an occlusion element at the distal end of the wire, the method comprising:
- positioning the proximal occluder in a vascular channel-occluding state within the vascular channel with its occlusion element at a first position proximal of a target site thereby occluding the vascular channel at the first position, the vascular channel having an inner wall;
- advancing the distal occluder through the lumen of the proximal occluder to position the occlusion element of the distal occluder in a vascular channel-occluding state within the vascular channel at a second position distal of the target site thereby occluding the vascular channel at the second position and thereby defining a region between the distal and proximal occluders;
- injecting an anti-proliferative drug into the region;
- advancing an interventional catheter over the wire of the distal occluder to position an interventional element comprising a stent structure configured to support and maintain pressure against the inner wall and an expandable balloon within the stent structure between the two occlusion elements;
- performing of a therapy using the interventional element while the distal and proximal occluders are in their vascular channel-occluding states and the anti-proliferative drug is in the region, wherein the performed therapy comprises:
  - (i) expanding the balloon to expand the stent structure against the inner wall of the vascular channel;
  - (ii) collapsing the balloon leaving the stent structure expanded against the inner wall to maintain pressure against the inner wall,
  - (iii) leaving the stent structure expanded against the inner wall for a period of time to inhibit elastic recoil of the inner wall while the balloon is collapsed to allow the occluded region to be bathed by the injected agent through the stent structure, and
  - (iv) collapsing the stent structure;
- removing the intervention catheter, interventional element, anti-proliferative drug, and other material from the region; and
- removing the catheter assembly from the vascular channel.

* * * * *